US008610086B2

(12) United States Patent
Wolleschensky et al.

(10) Patent No.: US 8,610,086 B2
(45) Date of Patent: Dec. 17, 2013

(54) INCREASED RESOLUTION MICROSCOPY

(75) Inventors: Ralf Wolleschensky, Jena (DE); Ingo Kleppe, Jena (DE); Gerhard Krampert, Jena (DE); Michael Kempe, Jena (DE)

(73) Assignee: Carl Zeiss Microscopy GmbH, Jena (DE)

(*) Notice: Subject to any disclaimer, the term of this patent is extended or adjusted under 35 U.S.C. 154(b) by 100 days.

(21) Appl. No.: 13/131,801

(22) PCT Filed: Nov. 14, 2009

(86) PCT No.: PCT/EP2009/008117
§ 371 (c)(1),
(2), (4) Date: May 27, 2011

(87) PCT Pub. No.: WO2010/060545
PCT Pub. Date: Jun. 3, 2010

(65) Prior Publication Data
US 2011/0226965 A1 Sep. 22, 2011

(30) Foreign Application Priority Data
Nov. 27, 2008 (DE) .......................... 10 2008 059 328

(51) Int. Cl.
*G01N 21/64* (2006.01)
(52) U.S. Cl.
USPC ...................................... 250/459.1
(58) Field of Classification Search
USPC .................. 250/458.1, 459.1; 356/317
See application file for complete search history.

(56) References Cited

U.S. PATENT DOCUMENTS

| 5,866,911 | A | 2/1999 | Baer |
| 6,633,432 | B2 | 10/2003 | Iketaki |
| 6,909,105 | B1 | 6/2005 | Heintzmann et al. |
| 7,626,695 | B2 | 12/2009 | Betzig et al. |
| 7,782,457 | B2 * | 8/2010 | Betzig et al. .................. 356/317 |
| 7,880,150 | B2 | 2/2011 | Hell et al. |
| 2008/0032414 | A1 | 2/2008 | Zhuang et al. |
| 2008/0088920 | A1 | 4/2008 | Wolleschensky |
| 2008/0158551 | A1 | 7/2008 | Hess |
| 2008/0182336 | A1 | 7/2008 | Zhuang et al. |
| 2009/0059360 | A1 | 3/2009 | Evans et al. |
| 2009/0134342 | A1 | 5/2009 | Hell et al. |
| 2010/0025567 | A1 | 2/2010 | Lueerssen |
| 2011/0036996 | A1 | 2/2011 | Wolleschensky et al. |

FOREIGN PATENT DOCUMENTS

| DE | 44 16 558 A1 | 8/1995 |
| DE | 103 25 460 A1 | 11/2004 |

(Continued)

*Primary Examiner* — David Porta
*Assistant Examiner* — Faye Boosalis
(74) *Attorney, Agent, or Firm* — Patterson Thuente Pedersen, P.A.

(57) ABSTRACT

Method for spatially high-resolution luminescence microscopy in which label molecules in a sample are activated to emit luminescence radiation comprising activating only a subset of the label molecules in the sample, wherein activated label molecules have a distance to the closest activated molecules that is greater or equal to a length which results from a predetermined optical resolution, detecting the luminescence radiation, generating a frame from the luminescence radiation, identifying the geometric locations of the label molecules with a spatial resolution increased above the predetermined optical resolution, repeating the steps and forming a combined image, and controlling the acquisition of the several frames by evaluating at least one of the frames or a group of the frames and modifying at least one variable for subsequent repetitions of the steps of generating frames for combining into an image.

14 Claims, 4 Drawing Sheets

(56) References Cited

FOREIGN PATENT DOCUMENTS

| | | |
|---|---|---|
| DE | 10 2006 009 831 A1 | 9/2007 |
| DE | 10 2006 021 317 B3 | 10/2007 |
| DE | 10 2008 009 216 A1 | 8/2009 |
| EP | 1 157 297 B1 | 11/2002 |
| EP | 1 921 440 A2 | 5/2008 |
| EP | 1 933 131 A1 | 6/2008 |
| EP | 1 985 995 A2 | 10/2008 |
| WO | WO 2006/127692 A2 | 11/2006 |
| WO | WO 2007/009812 A1 | 1/2007 |
| WO | WO 2008/032096 A2 | 3/2008 |
| WO | WO 2008/091296 A2 | 7/2008 |

\* cited by examiner

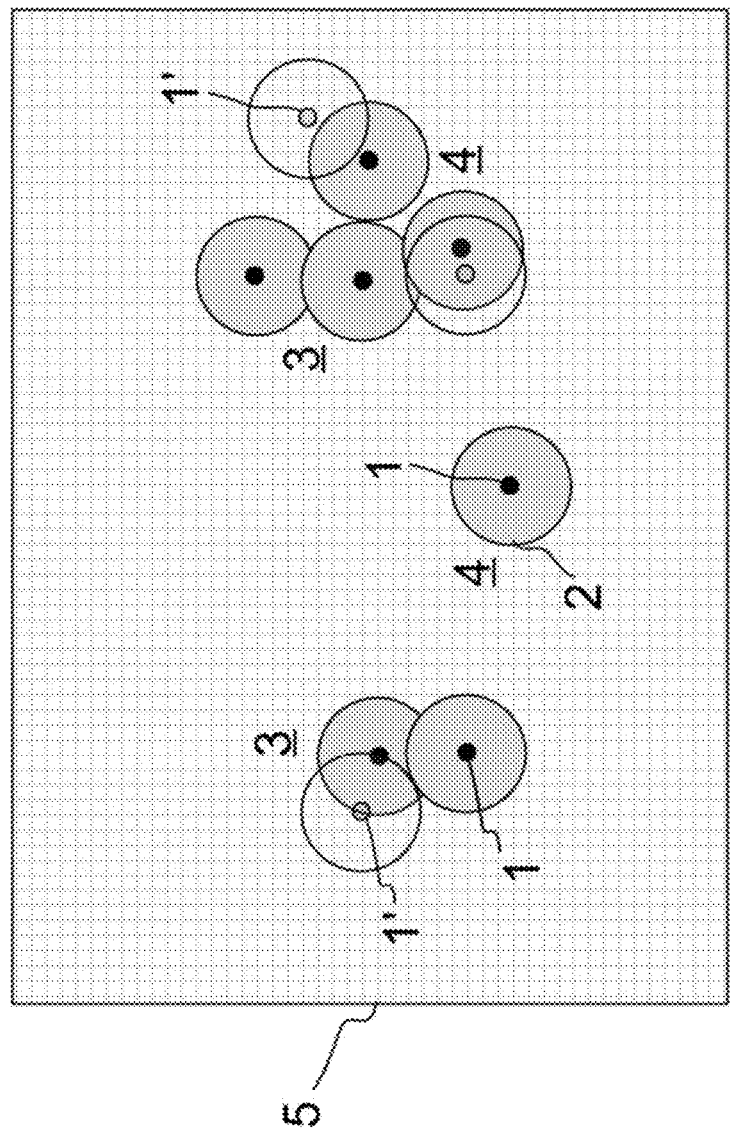
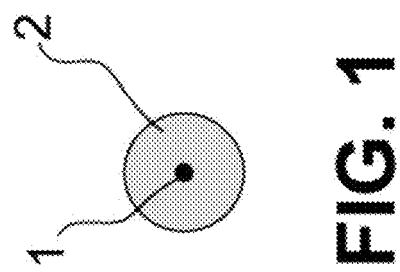

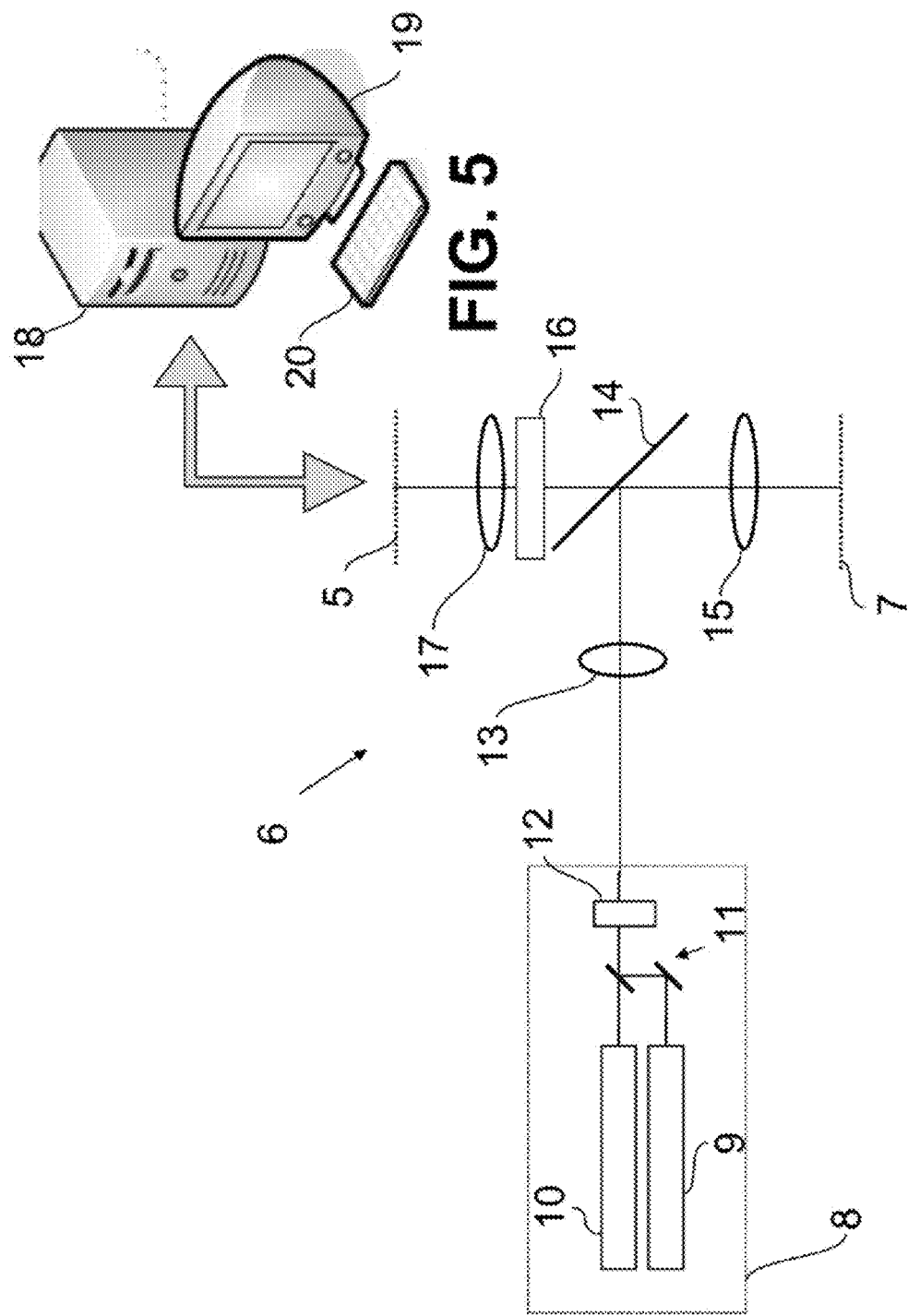

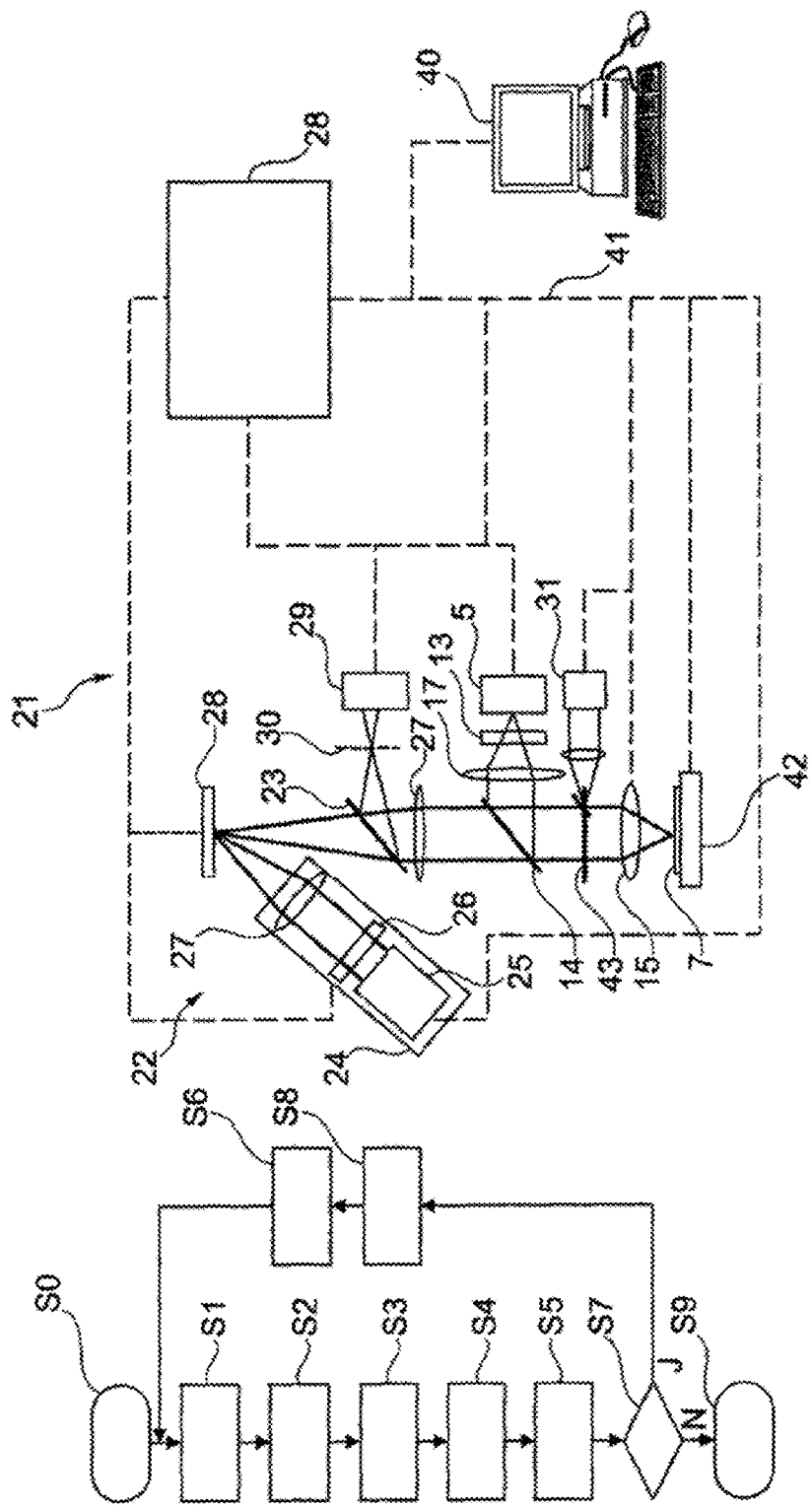

INCREASED RESOLUTION MICROSCOPY

PRIORITY CLAIM

The present application is a National Phase entry of PCT Application No. PCT/EP2009/008117, filed Nov. 14, 2009, which claims priority from German Application Number 10 2008 059 328.1, filed Nov. 27, 2008, the disclosures of which are hereby incorporated by reference herein in their entirety.

BACKGROUND OF THE INVENTION

Method for spatially high-resolution luminescence microscopy of a sample which is labelled with label molecules which can be activated by a switching signal such that they can be excited to emit particular luminescence radiation only in the activated state, wherein the method has the following steps:
a) introducing the switching signal onto the sample such that only a subset of the label molecules present in the sample are activated, wherein there are area parts in the sample in which activated label molecules have a distance to their closest neighbouring activated labelled molecules that is at least greater than or equal to a length which results from a predetermined optical resolution,
b) exciting the activated molecules to emit luminescence radiation,
c) detecting the luminescence radiation with the predetermined optical resolution and
d) generating a frame from the luminescence radiation recorded in step c), wherein the geometric locations of the label molecules emitting luminescence radiation are identified with a spatial resolution increased above the predetermined optical resolution,
wherein the steps are repeated several times and the several thus-obtained frames are combined into a complete image.

A standard field of use of light microscopy for examining biological preparations is luminescence microscopy. In this process, particular dyes (so-called phosphors or fluorophores) are used for the specific labelling of samples, e.g. of cell parts. The sample is, as mentioned, illuminated with illumination radiation realizing excitation radiation and the luminescence radiation excited thereby is recorded by suitable detectors. For this, a dichroic beam splitter is usually provided in the microscope in combination with block filters which split the luminescence radiation from the excitation radiation and enable an independent observation. Through this procedure, the imaging of individual, differently coloured cell parts is possible with the microscope. Of course, several parts of a preparation can also be simultaneously coloured with different dyes attaching specifically to different structures of the preparation. This method is called multiple luminescence. Samples which luminesce per se, thus without added dye, can also be surveyed.

Here, luminescence is understood, as is generally usual, as a generic term for phosphorescence and fluorescence, thus covers both processes. When fluorescence is mentioned here, it is to be understood pars pro toto and not to be limiting.

To examine samples, it is also known to use laser scanning microscopes (also LSM for short) which, from a three-dimensionally illuminated image, image by means of a confocal detection arrangement (when it is called a confocal LSM) or a non-linear sample interaction (so-called multiphoton microscopy) only that plane which is located in the focal plane of the objective. An optical section is produced and the recording of several optical sections at different depths of the sample then allows the generation, with the help of a suitable data-processing device, of a three-dimensional image of the sample which is composed of the different optical sections. Laser scanning microscopy is thus suitable for examining thick preparations.

Of course, a combination of luminescence microscopy and laser scanning microscopy is also used, in which a luminescent sample is imaged at different depth planes with the help of an LSM.

In principle, the optical resolution of a light microscope, also that of an LSM, is diffraction-limited by physical laws. For the optimum resolution within these limits, specific illumination configurations are known, such as for example a 4Pi arrangement or arrangements with standing-wave fields. Then, the resolution can be clearly improved, in particular in axial direction, over that of a standard LSM. Using non-linear depopulation processes, the resolution can be further increased to a factor of up to 10 compared with a diffraction-limited confocal LSM. Such a method is described for example in U.S. Pat. No. 5,866,911. Different approaches are known for the depopulation processes, for example as described in DE 4416558 C2, U.S. Pat. No. 6,633,432 or DE 10325460 A1.

A further method for increasing resolution is discussed in EP 1157297 B1. There, non-linear processes are utilized by means of structured illumination. The document mentions the saturation of the fluorescence as non-linearity. The described method claims to realize a shift of the object space spectrum relative to the transmission function of the optical system through a structured illumination. Specifically, the shift of the spectrum means that object space frequencies V0 are transmitted at a spatial frequency V0-Vm, wherein Vm is the frequency of the structured illumination. At a given spatial frequency maximally transmissible by the system, this enables the transfer of spatial frequencies of the object exceeding the maximum frequency of the transmission function by the shift frequency Vm. This approach requires a reconstruction algorithm for image generation and the utilization of several frames for an image. In this method also, it is to be considered disadvantageous that the sample is unnecessarily stressed with radiation in areas outside the detected focus, as the necessary structured illumination covers the whole sample volume. Moreover, this method cannot currently be used in the case of thick samples, as extra-focally excited fluorescence also reaches the detector as a background signal and thus dramatically reduces the dynamic range of the detected radiation.

A method which, independently of laser scanning microscopy, achieves a resolution beyond the diffraction limit is known from WO 2006127692 and DE 102006021317. This method, PALM for short, (Photo Activated Light Microscopy) uses a label substance which can be activated by means of an optical activation signal. Only in the activated state can the label substance be excited by excitation radiation to emit particular fluorescence radiation. Non-activated molecules of the label substance also emit after irradiation by excitation radiation no, or at least no noticeable, fluorescence radiation. The activation radiation thus switches the label substance into a state in which it can be excited to fluorescence. Different activation, e.g. of thermal type, is also possible. Therefore, the general term switching signal is used. In the PALM method, the switching signal is applied such that at least a certain proportion of the activated label molecules are spaced apart from neighbouring activated molecules such that they are separated, as measured by the optical resolution of the microscopy, or can be separated subsequently. The activated molecules are thus at least largely isolated. After recording the luminescence radiation, for these isolated molecules the centre of their radiation distribution caused in resolution-limited manner is then identified and the position of the molecules computationally determined from it with higher precision than the optical imaging itself allows. This increased resolution by computational determination of the centre of the diffraction distribution is also called "superresolution" in the state of the art. It requires at least some of the activated label molecules to be distinguishable, thus isolated, in the sample with the optical resolution with which the luminescence radiation is detected. For such molecules, the location information can then be achieved with increased resolution.

To isolate individual label molecules, the PALM method exploits the fact that the probability of a label molecule being activated after receipt of the switching signal of given intensity, e.g. a photon of the activation radiation, is the same for all molecules. Via the intensity of the switching signal and thus the number of photons which strike a unit area of the sample, it is thus possible to ensure that the probability of activating label molecules present in a given unit area of the sample is so small that there are enough areas in which only distinguishable label molecules emit fluorescence radiation within the optical resolution. The result of a suitable choice of the intensity, e.g. of the photon density, of the switching signal, is that, as far as possible, only label molecules isolated relative to the optical resolution are activated and subsequently emit fluorescence radiation. For these isolated molecules, the centre of the intensity distribution conditional on diffraction and thus the location of the label molecule is then identified computationally with increased resolution. To image the whole sample, the isolation of the label molecules of the subset is repeated by introducing activation radiation, subsequent excitation and fluorescence radiation imaging until, if possible, all label molecules were contained once in a subset and isolated within the resolution of the imaging.

The PALM method has the advantage that a high local resolution is necessary for neither the activation nor the excitation. Instead, both the activation and the excitation can be effected in wide-field illumination.

As a result, the label molecules are statistically activated in partial quantities by suitable choice of the intensity of the activation radiation. Therefore, a plurality of frames must be evaluated for the generation of a complete image of a sample in which the locations of all label molecules can be determined computationally with e.g. resolution lying beyond the diffraction limit. There can be up to 10,000 frames. The result of this is that large data quantities are processed, and the measurement lasts a correspondingly long time. The acquisition of a complete image alone requires several minutes, which is fixed essentially by the read-out rate of the camera used. The determination of the position of the molecules in the frames takes place by elaborate computational procedures, as described for example in Egner et al., Biophysical Journal, pp. 3285-3290, volume 93, November 2007. The processing of all frames and their combination into a high-resolution complete image, thus an image in which the locations of the label molecules are given with a resolution lying beyond the diffraction limit, typically lasts four hours.

SUMMARY OF THE INVENTION

A feature and advantage of the invention is to develop a PAL microscopy method such that a faster image production is achieved. Such is achieved by a method of the type named at the beginning, in which an adjustment of the acquisition of the several frames is effected by evaluating at least one frame or a group of the frames after carrying out step d) and modifying at least one variable of steps a-d for subsequent repetitions of steps a-d.

According to an embodiment of the invention, the acquisition of frames is now carried out in closed-loop controlled manner by evaluating a frame or a group of the frames and deriving from the evaluation a change in a variable which is relevant for the frame acquisition and modifying the corresponding variable accordingly.

An embodiment of the invention thus uses the particular nature of the imaging in the PALM method which progressively composes a high-resolution image from frames which each contain a subset of the molecules to be localized. At least one parameter for the image acquisition is optimized by the analysis of the frames, with the result that the acquisition of the whole image proceeds more quickly.

Many parameters are known in the state of the art which have previously been set as optimally as possible before the start of a PALM microscopy process. An adjustment of the image acquisition leading to a higher acquisition speed is effected now through the derivation of parameter optimizations during the image acquisition by evaluating a frame or a group of frames.

This has the advantage not only that the image acquisition proceeds more quickly overall, but also that the preparation time for the acquisition of an image is reduced. Less work is required to carefully identify the basic conditions for operating parameters prior to measurement in order to set the image-acquisition parameters right from the start to an optimum value. Now the optimum values result from the inventive adjustment during image acquisition.

A further advantage of the method according to an embodiment of the invention also lies in the fact that the boundary conditions which affect optimum image-acquisition parameters can now change during the image acquisition without affecting the acquisition duration. A simple example of this is the shifting of the sample to choose a different image section which can bring sample areas with a different concentration of label molecules and thus also an inevitably different optimum switching signal intensity into the current image field. The dynamic optimization method according to the invention guarantees through the adjustment of image-acquisition parameters as a result of a frame analysis that the optimum image-acquisition parameters are always quickly obtained even with varying boundary conditions and thus the image acquisition duration is reduced overall.

A variation in the boundary conditions can of course also occur due to stability limits of the aperture or the sample, e.g. focus drifts or temperature changes. These too now do not affect the acquisition duration as the image acquisition automatically reacts during adjustment.

The control according to an embodiment of the invention can also guarantee equipment-protection functions as well as the optimization. Thus, the highly sensitive detectors or cameras customarily used are easy to damage accidentally due to any incorrect filter settings, excitation power in relation to the fluorescence, etc. The adjustment during the acquisition of the total image prevents such damage.

In the case of the PALM image acquisition, the ratio of activation to de-activation (e.g. by bleaching) of the label molecules is closely linked with the total image-acquisition speed. It is already described in WO 2006/127692 A2 that an asynchronous activation and fluorescence excitation can serve to optimize the speed. DE 102006021317 B3 even gives percentages which relate to the portion of converted molecules which are separated from each other, thus disjunctive, relative to the optical resolution of the microscope. These fixed presets are superfluous with the invention and are at most starting values.

Values for optimum measurement parameters are derived from the frames and adjusted in respect of the image-acquisition speed or other criteria (e.g. the mentioned device protection) by corresponding changes in correcting variables during the subsequent frame acquisitions. A new frame acquisition cycle is thus carried out with settings which have been modified on the basis of the previous frame analysis and lead to more optimum (e.g. faster) acquisitions.

An acceleration on frame level need not necessarily occur. A reduced acquisition duration can above all also be achieved by requiring fewer frames, e.g. because the division into partial quantities is improved.

The distribution of the activated (and then later fluorescent) label molecules over the partial quantities is essential for an acceleration of the total image acquisition (each subset then corresponds to one frame). It is therefore provided in an embodiment of the invention that, for adjustment, a quality function is evaluated, and its value maximized, which function is directly or indirectly a measure of the proportion of the label molecules in the sample which are activated and have at least a distance to their closest neighbouring activated label molecules which distance can be resolved with the predetermined optical resolution. The quality function can in particular be a density measurement for the activated and thus fluorescent molecules. As homogeneous as possible a brightness of the fluorescent molecules in the frame is an indication of and thus a possible quality criterion for an image acquisition suitable in respect of the image acquisition speed.

The following consideration leads to a particularly suitable quality function: ideally, only a single label molecule contributes to the luminescence within a spatially resolvable area/volume. In principle, there can be only a whole-number quantity of molecules in a locally resolvable volume. Within a domain defined by the spatial resolution, only luminescence radiation which originates from either one, two, three, etc. label molecules can thus occur. A luminescence evaluation within a luminescent domain which is isolated from neighbouring luminescent domains thus allows it to be recognized by a threshold analysis whether there was one label molecule in the luminescent domain or more. It is therefore preferred in a development that luminescent domains which are isolated from neighbouring luminescent domains are identified for the evaluation of the quality function in each of the evaluated frames, a measure of the quantity of the luminescence radiation emitted by the respective isolated luminescent domain is identified for the isolated luminescent domains, and the proportion of the domains for which a measurement lying below a threshold has been identified is given as a value of the quality function. The threshold is expediently to be chosen such that it lies slightly above the luminescence quantity measurement which corresponds to a domain in which only one label molecule emitted luminescence radiation.

The measure of the emitted luminescence radiation can be the integral of the luminescence intensity over the identified domain. Other parameters are equally possible. If the maximum of the luminescence intensity occurring in the luminescent domain is used as a measure, it is shown that the method is particularly immune to defocusing.

Background noise naturally always plays a role during the acquisition of an image. Where isolated domains are mentioned in this description, this is therefore to be understood as meaning that the recorded intensity drops below a threshold which, however, need not necessarily be zero because of background noise.

It is therefore preferred that the measure of the quantity of the emitted luminescence radiation is an integral above the luminescence radiation intensity or the maximum of the luminescence radiation intensity, in each case in the identified isolated luminescent domain.

A further possible indicator for the density of the luminescent label molecules is the distance that a luminescent domain has to the closest neighbouring luminescent domain. This distance can be measured for example by a suitable circular fit around an identified luminescent domain.

Preferably, the minimum distance of an identified isolated luminescent domain to the closest neighbouring luminescent domain is determined, and the proportion of the domains the minimum distance between which is greater than a resolvable minimum distance preset by the predetermined optical resolution or a preset multiple of this minimum distance is taken as a value of the quality function.

An alternative approach is to check whether the total recorded radiation around a local fluorescence intensity maximum lies within a particular distance around the local maximum. If the local intensity maximum comes from a luminescent label molecule and this label molecule is isolated, then beyond the resolution limit the luminescence intensity will have dropped to a minimum value defined by the background noise. If, on the other hand, such a threshold is not yet reached with a given distance around the local maximum, either the maximum comes from more than one luminescent label molecule, or there is a further luminescent label molecule at a non-optically resolvable distance.

It is therefore preferred that, to evaluate the quality function, luminescent domains which are isolated from neighbouring luminescent domains are identified in each of the evaluated frames and, for each of these isolated luminescent domains, the size of this luminescent domain is identified relative to a measure preset on basis of the optical resolution and that the proportion of the total surface of the frame is used as a measure of the quality function, the luminescent domains have an extent around their local maximum which is smaller than a size derived from the optical resolution, in particular smaller than a preset multiple of the smallest resolvable length.

For these two variants, a circle can be placed around the geometric centre or the local intensity maximum of the respective luminescent domain, within which the luminescence intensity must have dropped to a particular minimum value, or which extends as far as the closest neighbouring luminescent domain. The proportion of the domains in which the luminescence has fallen below the maximum value within a preset circle radius, or the proportion of the domains of which the circle radius is greater than the resolvable minimum distance or is a preset multiple of the minimum distance, is taken as a value of the quality function.

In principle, the method can analyze every frame individually, i.e. it can switch from frame to frame between the described image evaluation approaches. However, in terms of the stability of the control, it is preferred that the same type of frame evaluation is constantly carried out. It is further advantageous, in respect of stability, if a batch of successive frames is evaluated, luminescent domains which are isolated from neighbouring luminescent domains are isolated in each of the evaluated frames, and the proportion of the luminescent domains which luminesce precisely in one frame of the group is taken as a value of the quality function.

The controlled correcting variables can comprise at least one of the following parameters: filtering, polarization filtering, amplification, detector temperature, integration duration, choice of detection field, position and size of focus during detection of the luminescence radiation, power, pulse shape, pulse frequency, wavelengths, irradiation duration, choice of irradiation field, penetration depth of a TIRF illumination, position and size of a focus during the introduction of the switching signal or during the excitation of the activated molecules.

At least one of the following variables can be recorded and evaluated in the image evaluation: bleaching rate of the label molecules, excitation and emission spectra of the label molecules, life of luminescence states of the label molecules, activation threshold of the label molecules, flash frequency of the label molecules, period for which individual label molecules are visible on average, number of luminescent label molecules coinciding within the optical resolution, number of collected photons per luminescent label molecule, number of activated label molecules per frame, average localization accuracy of the label molecules per frame.

In an embodiment of the invention, a further optimization approach within the framework of the closed-loop control checks how long a molecule fluoresces for. Ideally, an activated and excited label molecule contributes to precisely only one frame, as the probability that as many label molecules as possible are disjunctive is then at its greatest. Molecules which can be excited to luminescence radiation over more than one frame could combine with label molecules appearing in the next step, i.e. newly activated, to form a not separable luminescent domain. This is not desired. The described variant therefore optimizes the number of individual molecules which emit luminescence radiation over precisely one frame. During a de-activation of label molecules by bleaching, i.e. by an excitation that is so strong that the label molecule is permanently or at least temporarily unable to be excited to luminescence again, the optimization of the label molecules which emit luminescence radiation for a frame can be achieved by increasing the excitation intensity. This variant is an example showing that the correcting variable need not automatically be involved in the activation of the label molecules, but can definitely also affect the excitation.

In an embodiment of the invention, a further variable that is particularly advantageous for increasing the image acquisition speed is the synchronization of detection and of activation or excitation. In particular, dye properties, such as e.g. bleaching rate, switching cycles, excitation and emission spectra, life, etc. are important for optimum PALM image acquisitions. On average, the duration for which an individual label molecule stays in the state in which it can be excited to luminescence should be matched to the detection of the luminescence radiation in step c) and there in particular to an illumination duration such that the label molecule emits its luminescence radiation as much as possible within a detection step c) and does not sometimes fall into detection steps for two successive frames. As most of the luminescent label molecules are visible only in very few frames of a detection step at an optimized image-acquisition speed, the two boundary frames (frames in which a molecule starts or ends the luminescence) represent significant proportions of the luminescence signal collected overall. In order to make the best possible use of the frames during the image acquisition and thus e.g. the integration time of a CCD camera, a temporally modulated intensity of the activation radiation is therefore to be carried out synchronized to the detector in step c), e.g. to the operation of a camera, with the result that the probability of excitation of a molecule lies as far as possible at the start of a frame.

For some types of photo-switchable proteins, their average excitability range prior to a reversible or irreversible de-activation is a function of the illumination conditions. The luminescence radiation of the photo-switchable proteins differs from a background signal in their bleaching behaviour. A previously identified bleaching behaviour can thus be used to distinguish the label molecules from background radiation. Alternatively, the life can be used. This information can be used to preset limits for the adjustment range.

It is understood that the features named above and still to be explained below can be used not only in the given combinations, but also in other combinations or alone, without departing from the framework of the present invention.

DESCRIPTION OF THE DRAWINGS

The invention is explained in further detail below by way of example using the attached drawings which also disclose features essential to the invention. There are shown in:

FIG. 1 a schematic representation of an activated label molecule in a resolution-limited volume;

FIG. 2 a schematic representation of the imaging of different activated and non-activated label molecules onto a spatially resolving detector, FIG. 3 a flowchart for the image generation in the PALM method, FIG. 4 explanatory representations relating to the flowchart of FIG. 3 concerning label molecules imaged onto the detector of FIG. 2, FIG. 5 a schematic representation of a microscope for PAL microscopy, FIG. 6 a flowchart for the image generation in the PALM method with adjustment of image production parameters and FIG. 7 a microscope similar to that of FIG. 4, developed for the selection of sample areas.

DETAILED DESCRIPTION

Figure 3:
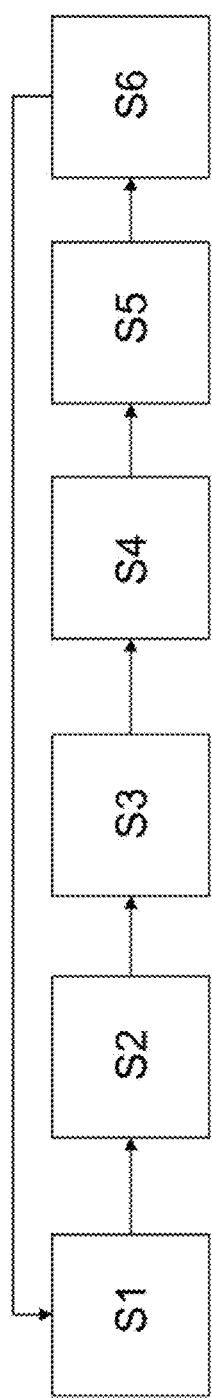

FIG. 1 schematically shows a label molecule 1 which has been excited to fluorescence. Of course, fluorescence detection requires a plurality of excitations, as each excitation delivers precisely one fluorescence photon and radiation detection requires an integration over many fluorescence photons. Due to the laws of physics, the fluorescence radiation emitted by the label molecule 1 can be detected in a microscope with only a limited optical resolution. Even if the microscope reaches the diffraction limit of the optical resolution, the photons of the fluorescent label molecule 1 are still always scattered due to diffraction and thus detected as an Airy disk 2. The microscope thus depicts in principle a larger object which is illustrated in FIG. 1 by the Airy disk 2, instead of the geometric extent of the label molecule 1 which is drawn schematically in FIG. 1 as a black circle. The size of the Airy disk 2 depends on the quality of the microscopy device used and is defined by the half width of the point-spread function of the optical imaging. Of course, it is not actually a two-dimensional object, but a diffraction volume which the fluorescence photons enter. However, in the two-dimensional representation of FIG. 1, this volume appears as a disk. The term Airy disk is therefore taken quite generally here to mean a maximum resolution volume which the lens system used can achieve. However, the lens system used need not necessarily operate at the diffraction limit, even if this is to be preferred.

In order to now be able to locate the label molecule 1 more precisely within the Airy disk 2, the PALM method already described in general above is used. The method activates individual label molecules, wherein by the term activation is meant in this description, quite generally, the activation of particular luminescence properties of the label molecules, thus both a switching-on of the luminescence excitability and a change in the luminescence emission spectrum, which corresponds to the switching-on of particular luminescence properties. In the embodiment described here, the activation is effected by optical activation radiation. However, other non-optical activation mechanisms are equally possible.

The activation is effected now such that there are at least a few activated molecules the centre of which does not lie in the Airy disk of other activated molecules, i.e. which can still just be distinguished under the optical resolution given.

FIG. 2 schematically shows an exemplary situation on a detector 5 which integrates over the photons in locally resolving manner. As can be seen, there are areas 3 in which the Airy disks of neighbouring label molecules overlap. However, as can be seen in the left-hand area 3 of FIG. 2, only those label molecules which have previously been activated are relevant here. Non-activated label molecules 1' do not emit the particular fluorescence radiation which is collected on the matrix detector 5, thus do not play a role.

Label molecules 1 lie in the areas 4, e.g. the area 4 located in the middle of the matrix detector 5, such that their Airy disk 2 does not overlap with an Airy disk of another activated label molecule 1. The right-hand area of the matrix detector 5 shows that areas 3 in which Airy disks of activated label molecules overlap can definitely lie next to areas 4 in which this is not the case. The right-hand area 4 also makes it clear that having an activated label molecule 1 next to a non-activated label molecule 1' does not play a role in the detection, as such a label molecule 1' does not emit the fluorescence radiation detected by the matrix detector 5, thus does not fluoresce.

For the acquisition of an image containing more detail than the optical resolution predetermined by means of equipment allows, which is a high-resolution image within the meaning of this description, the steps schematically represented in FIG. 3 are now used.

In a first step S1, a subset of the label molecules are activated by means of a switching signal; they are thus switched from a first state in which they cannot be excited to emit the particular fluorescence radiation into a second state in which they can be excited to emit the particular fluorescence radiation. Of course, the activation signal can also effect a selective de-activation, thus a reverse procedure can also be used in step S1. It is essential that, after step S1, only a subset of the label molecules can be excited to emit the particular fluorescence radiation. Activation or de-activation (only the case of activation is described below, for the sake of simplification) takes place depending on the label molecules used. With a dye such as e.g. DRONPA, PA-GFP or reversibly switchable synthetic dyes (such as Alexa/Cyan constructs), the activation takes place by optical radiation, thus the switching signal is switching radiation.

Figure 4:
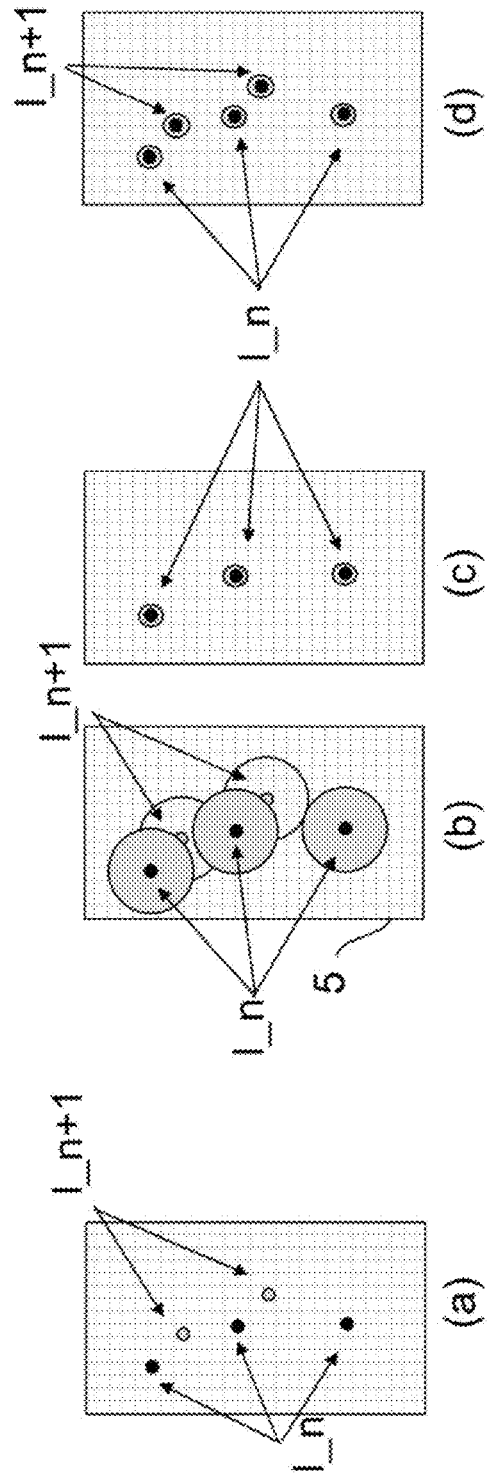

FIG. 4, represented below FIG. 3, shows in the sub-image a the state after step S1. Only a subset of the label molecules $1\_n$ is activated. The label molecules of this subset are represented by a solid black spot. The rest of the label molecules have not been activated in this step. They are denoted by $1\_n+1$ in sub-image a of FIG. 4.

Label molecules which have been activated can then be excited in a second step S2 to emit fluorescence radiation. Fluorescent proteins known from the state of the art, such as PA-GFP or also DRONPA, are preferably used as fluorescent dyes. The activation takes place in the case of such molecules with radiation in the range of 405 nm, the excitation to fluorescence radiation at a wavelength of about 488 nm, and the fluorescence radiation lies in a range above 490 nm.

In a third step S3, the emitted fluorescence radiation is detected, for example by integration over the recorded fluorescence photons, with the result that the situation represented in the sub-image b of FIG. 4, located at the bottom, occurs on the matrix detector 5. As can be seen, the Airy disks of the activated label molecules $1\_n$ do not overlap. The size of the Airy disks is determined by the optical resolution of the imaging onto the matrix detector 5. In addition, (theoretical) Airy disks of fluorescence molecules which belong to the non-activated subset $1\_n+1$ are shown in sub-image b of FIG. 4. As these non-activated label molecules do not emit fluorescence radiation, no fluorescence radiation lying in their (theoretical) Airy disks interfere with the detection of the fluorescence radiation of the subset $1\_n$ of the activated label molecules.

In order that as few Airy disks as possible overlap in the subset $1\_n$ so that the label molecules can no longer actually be distinguished, the activation energy is adjusted such that the subset $1\_n$ accounts for only a comparatively small proportion of the total quantity of the label molecules, with the result that statistically many label molecules can be distinguished relative to the volume resolvable with the optical arrangement.

In a fourth step S4, the position of the fluorescent label molecules is identified computationally from the diffraction distribution of the fluorescence disks, whereby the resolution with which the position of the activated label molecules is known is sharpened beyond the resolution of the optical arrangement, as the sub-image c of FIG. 4 shows.

As an alternative to a computational determination, it is perfectly possible in principle to amplify the recorded fluorescence radiation non-linearly and thus to sharpen the resolution beyond the optical arrangement with reduced effort. The non-linear amplification can be described for example by the function $S=A \cdot F^N$ (equation 1) or $S=A \cdot \exp^{F/w}$ (with $w=10^{-N}$ (equation 2)), wherein F is the amplitude of the fluorescence signal, A is a scaling factor and N is an integer greater than 1. A strong non-linear dependency of the parameter S on F, thus e.g. high values for N in the equations 1 or 2, is particularly advantageous. Of course, other functions can also be used. In principle, the non-linearity is preferably chosen such that the half-width of the Airy disk corresponds to a sought spatial resolution for the location information of the label molecules. In addition to a non-linear amplification, a non-linear attenuation can also be used. Fluorescence signals of low amplitude or intensity are here attenuated, whereas strong signals remain at least largely unattenuated. Of course, a combination of non-linear amplification and attenuation can also be used.

A fifth step S5 now combines the label molecules the position information of which is precisely known into a frame the spatial resolution of which is increased beyond the optical resolution. However, it contains only information on the previously activated subset of the label molecules.

In a sixth step S6, the frame is placed into a total image in known manner. Then the method returns to step S1, wherein the hitherto fluorescent molecules have to be de-activated again. A de-activation can be achieved, depending on the type of label molecule, by a separate radiation or by fading of the activation state. It is also possible to bleach already imaged label molecules by excitation radiation.

A further frame which contributes to the total image is thus obtained with each pass. In the next pass, a different subset of the label molecules is activated, e.g. the subset $1\_n+1$ represented in FIG. 4.

The repeated passes through steps S1 to S6 builds up the total image from frames of the individual passes which indicate the locations of the label molecules with a spatial resolution that is sharpened compared with the resolution of the optical imaging. Through a corresponding number of repetitions, a high-resolution total image thus progressively builds up. The reduction of the Airy disk takes place in the method preferably in all three spatial dimensions if several image stacks which are spaced apart in z-direction are recorded. The complete image then contains the location information of the label molecules highly resolved in all three spatial directions.

FIG. 5 schematically shows a microscope 6 for the high-resolution imaging of a sample 7. The sample is labelled for example with the dye DRONPA (cf. WO 2007009812 A1). For the activation as well as for the fluorescence excitation, the microscope 6 has a radiation source 8 which has individual lasers 9 and 10 the beams of which are combined via a beam merger 11. The lasers 9 and 10 can emit radiation for example at 405 nm (activation radiation) and 488 nm (fluorescence excitation and de-activation). Dyes (e.g. the dye called DENDRA (cf. Gurskaya et al., Nature Biotech., volume 24, pp. 461-465, 2006)) with which the activation and fluorescence excitation can take place at one and the same wavelength are also known. One laser is then enough.

An acousto-optic filter 12 is used for the wavelength selection and for the rapid switching or attenuation of individual laser wavelengths. A lens system 13 focuses the radiation into a pupil of an objective 15 via a dichroic beam splitter 14, with the result that the radiation of the radiation source 8 is incident on the sample 7 as wide-field illumination.

Fluorescence radiation arising in the sample 7 is collected via the objective 15. The dichroic beam splitter 14 is designed such that it allows the fluorescence radiation to pass, with the result that it passes through a filter 16 into a tube lens 17, with the result that the fluorescent sample 7 is imaged as a whole onto the detector 5.

To control the operation of the microscope 6, a control device is provided, here formed as a computer 18 with display 19 and keyboard 20. The method steps S2 to S6 take place in the computer 18. The image rate of the matrix detector is decisive for the total measuring time, with the result that a matrix detector 5 with as high an image rate as possible is advantageous in order to reduce the measuring time.

The described method realizes, with the microscope 6, a complete image which has e.g. a spatial resolution increased by a factor of 10 compared with the optical resolution of the microscope. The optical resolution of the microscope 6 can be for example 250 nm laterally and 500 nm axially.

For the operation of the microscope 6 for PAL microscopy, it is of course essential that the percentage of label molecules 1 which are isolated is as high as possible, as few frames are then necessary and the image acquisition speed is optimum. The control device in the form of the computer 18 therefore carries out within the framework of the method described using FIG. 3 a closed-loop control which may be explained with reference to FIG. 6:

FIG. 6 shows the method, wherein the steps already represented in FIG. 3 and explained using this figure are provided with the same reference numbers, thus avoiding the need to repeat description. In addition to a starting step S0 and an end step S9 as well as an inquiry S7, also implicitly provided in FIG. 3 in the method, as to whether the image acquisition is completed, FIG. 6 also shows a step S8 which represents a frame evaluation and variable modification. In this step S8, a previously generated frame is evaluated and the evaluation leads to a modification of operating parameters during the introduction of the switching signal (step S1), during the fluorescence excitation (step S2) and/or during the fluorescence detection (step S3). The step S8 need not be performed after each generation of a frame. Depending on the control speed sought and justifiable effort of control, the step S8 can also be performed only after every second, third, etc. pass, wherein a single frame or the whole group of frames generated since step S8 was last performed can then be used in the evaluation.

The frame evaluation generates a quality function which is e.g. a measure of the separation of the fluorescent label molecules. The approaches previously described in general can here be used individually or in any desired combinations.

In addition, it may also be mentioned that the frame evaluation can be directed towards tags added explicitly to the sample which do not serve to tag sample elements to be analyzed, but are evaluated only to optimize the frame acquisition.

In FIG. 7, a development of the microscope 6 of FIG. 5 is represented which, in addition to the described PALM method, can also simultaneously perform standard microscopy methods, i.e. microscopy methods having a diffraction-limited resolution. Elements of the microscope 21 shown in FIG. 7, which correspond to those of the microscope 6, are provided with the same reference numbers. The above description applies to them in equal measure, unless otherwise noted.

The microscope 21 is modular in structure, and it is described in a quite complete version to better illustrate the invention. However, a reduced structure with few modules is also possible. The modular structure is also not necessary; a one-piece or non-modular design is likewise possible. The microscope 21 is constructed on the basis of a conventional laser scanning microscope and records the sample 7.

For all microscopy methods the radiation passes through the objective 15. Via the beam splitter 14, the objective 15 images the sample 7 together with the tube lens 17 onto the detector 5 which is generally an area detector. In this respect, the microscope 21 has a conventional light microscope module, and the beam path from the sample 7 through the objective 15 and the tube lens 17 to the detector 5 corresponds to a conventional wide-field detection beam path. The beam splitter 14 is preferably exchangeable in order to be able to switch between beam splitters with different dichroic properties or achromatic beam splitters according to US 2008/0088920.

Also connected to the beam path to the objective 21 is a laser scanning module 22, the LSM illumination and detection beam path of which is coupled into the beam path to the objective 15 via a further, likewise preferably exchangeable beam splitter 23. The laser scanning module 22 has several components. A laser device 24 comprises a laser 25 which acts on a driven phase modulator 26. A lens system 27 then focuses the radiation onto a DMD 28. For the detection arm of the LSM module, a LSM detector 29 is shown by way of example in FIG. 4, as well as a confocal diaphragm 30 located in an intermediate image plane. The detection arm is coupled in through the beam splitter 23. The beam splitters 14 and 23 are optionally combined into one beam splitter module 12, whereby there is then the possibility of switching them depending on use.

The laser device 24 of the laser scanning module 22 generates radiation necessary for the PALM operation analogously to the radiation source 8, can thus emit radiation at different wavelengths or comprises several laser sources.

An optional TIRF illumination module 31 which realizes a TIRF illumination that can be switched on is provided as further illumination module. The TIRF illumination module 31 generates radiation or obtains it from a radiation source, e.g. a laser via an optical fibre. The TIRF illumination module 31 is formed to radiate TIRF illumination at the objective 15 at an adjustable angle to the optical axis of the objective 13. In this way, the angle of the total reflection at the cover glass can be easily guaranteed. The TIRF illumination module 31 can also operate as a wide-field illumination source if it radiates an illumination beam on the optical axis.

The modules and drives as well as detectors of the microscope 1 are all connected to a control device 32 via lines (drawn as dashed lines) not identified more precisely. This connection can take place for example via a data and control network 33. The control device 32 controls the microscope 21 in different operating modes.

The control device 32 is formed to perform standard microscopy, i.e. wide-field microscopy (WF), laser scanning microscopy (LSM) and also total internal reflection fluorescence microscopy (TIRF), at the microscope 21 and to combine these with the high-resolution microscopy method PALM.

A computer having a display 19 which computer is also connected to the data and control network 33 via which the control device 32 is connected to the individual components of the combination microscope 21 is further represented by way of example in FIG. 7.

A sample stage 42 on which the sample 7 can be moved under control of the control device 32 is also represented in FIG. 7. Such a sample stage is of course, like all other details of FIG. 7 as well, also possible in the microscope 6 of FIG. 5.

The microscope 21 further allows an improved activation and/or excitation:

Firstly, regions of particular interest (ROI) can be selected by a user himself, supported by the computer or automatically, and the control of the activation radiation from the laser device 24 is influenced accordingly. For this, the DMD 28 is used which is illuminated over its whole surface by laser radiation from the laser 24. The individual mirrors of the DMD are now set such that only the selected ROIs are illuminated and an optical activation of the label substance (e.g. DRONPA or EOS-FP) is thus carried out only in these regions. The remaining mirrors of the DMD 28 remain in a switched-off position, and the radiation directed onto them is absorbed in a beam trap (not shown).

Secondly, the switched-on DMD mirrors can be time-modulated in order to continuously attenuate the activation power. The activation power can thereby be efficiently matched, particularly advantageously for the PALM method, to the molecule concentration with the result that, regardless of the local label molecule concentration, the activated molecules are located at a distance greater than the optical resolution of the microscope 21. The sample 7 can thus be surveyed particularly quickly, in particular as the activation intensity and/or spatial distribution can be suitably set within the framework of the described control. A local adjustment is particularly advantageous if strong local concentration changes occur, e.g. bright areas are present next to faintly stained areas. Locally different bleaching of label substances, which can occur e.g. because of structural variations in the sample 7, can further lead to local concentration changes which can now be particularly advantageously balanced with the activation control.

In the case of an activation in pre-defined ROI by means of the optional phase modulator 26, the ROI pattern can be imaged preformed alternatively or additionally onto the whole DMD 28 which then still carries out only a fine tuning. Thus the power of the laser 25 is almost completely used to activate label molecules in the sample 7. For that purpose, the phase modulator 26 is arranged in a pupil plane before the DMD 28 (seen from the laser 25) and is located at a distance to the focal length of the lens system 27 (which can also be realized by an individual lens). The DMD 28 is in turn located at the same distance after the lens system 27. Alternatively, the DMD 28 can also be omitted if for example the ROI selection is effected through the phase modulator 26 and the intensity of the laser source 25 is globally adjusted, e.g. by an intensity modulator downstream of the laser or by a direct intensity modulation of the laser 25. The intensity modulation is of course perfectly possible in principle in the described adjustment, even with differently designed microscopes.

With the help of the combination microscope 1 of FIG. 5 or 7, it is additionally possible to record, sequentially or simultaneously, LSM microscopy images and PAL microscopy images and to adjust the acquisition of the PAL microscopy images not only by means of information which has been obtained from one or more PALM frames, but also with data which have been generated from the LSM microscopy image.

The variables used to adjust the frame acquisition can be:
1. On the detection side:
   a. frequency bands/filters;
   b. amplification factors (e.g. Preamp Gain, EMCCD Gain);
   c. temperature of a detector;
   d. integration time of the detection;
   e. detection modes (e.g. photon count, baseline clamp) of the detection;
   f. read-out of only specific ROIs;
   g. polarization of the detected radiation;
   h. focus
2. On the excitation side:
   a. radiated excitation and/or activation radiation;
      i. pulse shape or CW;
      ii. power and pulse frequency;
      iii. wavelengths;
   b. radiation duration;
   c. excitation locally specific (pixel-by-pixel) or of specific ROIs or over areas;
   d. size of the illumination field;
   e. penetration depth in the case of TIRF illumination;
   f. focus position.
3. On the sample side:
   position of the observation region in the sample.

The frame evaluation can in particular provide information on the following parameters:
1. dye properties:
   a. bleaching rate;
   b. excitation/emission spectra;
   c. life;
   d. activation threshold;
   e. photon rate per molecule;
   f. flash frequency;
2. imaging/image properties:
   a. form and intensity of the measured point-spread functions, not only of the individual activated molecules but also of tags possibly embedded in the sample (e.g.: gold beads), difference in form and intensity of the measured PSFs with different colours;
   b. period for which individual molecules are visible on average;
   c. number of molecules activated per point-spread function which overlap in space and time (measure of "activation density");
   d. label molecule density (locally defined), measured by e.g. intensities of the fluorescence at a further wavelength. This is possible for dyes which switch/convert between two fluorescent states (e.g. tdEos). Label molecule density can in addition also be determined via fluorescence at the measurement wavelength, by e.g. an early image on which various already converted, but not bleached, label molecules can be seen. In addition, the label density can also be estimated via further correlated colourings or other contrast methods;
e. number of collected photons per molecule;
f. number of activated molecules per frame;
g. average location accuracy of the molecules per frame;
h. to protect the camera, for one thing the combination of used filters and excitation lines of individual laser wavelengths can be used, but for another also the measured intensities of detected fluorescence at other wavelengths;
i. correlation of fluorescence images acquired with possibly different excitation wavelengths or correlation with images from further contrast methods such as e.g. DIC.

The invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. Method for spatially high-resolution luminescence microscopy of a sample which is labelled with label molecules which can be activated by a switching signal such that the label molecules can be excited to emit particular luminescence radiation only in the activated state, comprising:
   a) introducing the switching signal onto the sample such that only a subset of the label molecules present in the sample are activated, wherein there are area parts in the sample in which activated label molecules have a distance to their closest neighbouring activated label molecules that is at least greater than or equal to a length which results from a predetermined optical resolution,
   b) exciting the activated molecules to emit luminescence radiation,
   c) detecting the luminescence radiation with the predetermined optical resolution,
   d) generating and acquisitioning a frame from the luminescence radiation recorded in step c), wherein the geometric locations of the label molecules emitting luminescence radiation are identified with a spatial resolution increased above the predetermined optical resolution,
   wherein the steps are repeated several times and the several, thus-obtained frames are combined into a total image, and
   controlling the acquisition of the several frames by evaluating at least one of the frames or a group of the frames after step d) and modifying at least one variable of steps a-d for subsequent repetitions of steps a-d.

2. Method according to claim 1, wherein, during the step of controlling the acquisition, said step includes evaluating a quality function and maximizing a value thereof, and choosing the quality function such that it is directly or indirectly a measure of the proportion of the label molecules in the sample which are activated and have at least the distance to their closest neighbouring activated label molecules that can be resolved with the predetermined optical resolution.

3. Method according to claim 2, wherein the quality function is a density measurement for the activated molecules.

4. Method according to claim 3, further comprising identifying luminescent domains which are isolated from neighbouring luminescent domains for evaluating the quality function in each of the evaluated frames, a measure of the quantity of the luminescence radiation emitted by the respective isolated luminescent domain being identified for the isolated luminescent domains, and the proportion of the domains for which a measure lying below a threshold occurs being taken as a value of the quality function.

5. Method according to claim 4, wherein the measurement of the quantity of the emitted luminescence radiation is an integral over the luminescence radiation intensity or the maximum of the luminescence radiation intensity.

6. Method according to claim 3, for evaluating the quality function, further comprising identifying luminescent domains which are isolated from neighbouring luminescent domains are identified in each of the evaluated frames, determining for each of these isolated luminescent domains a minimum distance to the closest neighbouring luminescent domain, taking as a value of the quality function the percentage of the domains of which the minimum distance of which is greater than a resolvable minimum distance or a preset multiple of this distance and defining the resolvable minimum distance on basis of the predetermined optical resolution.

7. Method according to claim 6, wherein, in determining the minimum distance, a circle is placed around the geometric centre of the respective luminescent domain which circle extends as far as the closest neighbouring luminescent domain, and taking as a value of the quality function the percentage of the domains of which the circle radius greater than the distance or a preset multiple of the distance.

8. Method according to claim 2, wherein when a group of successive frames is evaluated, identifying luminescent domains which are isolated from neighbouring luminescent domains in each of the evaluated frames, and taking as a value of the quality function the percentage of the luminescent domains which luminesce in precisely one frame of the group.

9. Method according to claim 1, wherein the variables comprise at least one of the following parameters:
   filtering, polarization filtering, amplification, detector temperature, integration duration, choice of detection field, position and size of focus during the detection of the luminescence radiation; and
   power, pulse shape, pulse frequency, wavelengths, radiation duration, choice of radiation field, penetration depth of a TIRF illumination, position and size of focus during introduction of the switching signal or during the excitation of the activated molecules.

10. Method according to claim 1, wherein at least one of the following variables is recorded and evaluated in the image evaluation: bleaching rate of the label molecules, excitation and emission spectra of the label molecules, life of luminescence states of the label molecules, activation threshold of the label molecules, blinking rate of the label molecules, period for which individual label molecules are visible on average, number of luminescent label molecules coinciding within the optical resolution, number of collected photons per luminescent label molecule, number of activated label molecules per frame, average location accuracy of the label molecules per frame.

11. Method according to claim 1, further comprising recording at several excitation wavelengths further fluorescence images having ordinary optical resolution and the correlating frames with the fluorescence images for the evaluation.

12. Method according to claim 11, further comprising acquiring the further fluorescence images during the acquisition of the frames.

13. Method according to claim 1, further comprising recording with contrast methods further fluorescence images having ordinary optical resolution and correlating the frames with the fluorescence images for the evaluation.

14. Method according to claim 13, further comprising acquiring the further fluorescence images during the acquisition of the frames.

* * * * *